US00PP35658P2

(12) United States Plant Patent
Scheiber et al.

(10) Patent No.: US PP35,658 P2
(45) Date of Patent: Feb. 20, 2024

(54) ***HYDRANGEA* PLANT NAMED 'PAN1782HYDR'**

(50) Latin Name: *Hydrangea paniculata*
Varietal Denomination: Pan1782hydr

(71) Applicant: The Conard Pyle Company, West Grove, PA (US)

(72) Inventors: Sloane Michele Scheiber, West Grove, PA (US); Laura Lara Santisteban, West Grove, PA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 18/091,537

(22) Filed: Dec. 30, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP12,874 P2 * 8/2002 Zwijnenburg, Jr. ..... A01H 6/48 Plt./250
PP16,166 P2 12/2005 Van Huylenbroeck

OTHER PUBLICATIONS

"Star Roses and Plants 2023 Catalog Woody Ornamentals & Edibles", Aug. 2022, pp. 9, 10, 17, 59, 85, 90, 93, and 95, Including p. 1, cover and back pages.

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of *Hydrangea* plant, referred to by its cultivar name, 'Pan1782hydr', is disclosed. The new variety forms attractive, right white colored inflorescences which age from light pink to dark antique pink. Very strong stems which prevent flopping are formed. A moderately vigorous, dense, and compact growth habit is displayed. The new variety is well suited for providing attractive ornamentation in the landscape.

1 Drawing Sheet

Latin name of genus and species of plant claimed: *Hydrangea paniculata.*

Variety denomination: 'Pan1782hydr'.

STATEMENT REGARDING PRIOR DISCLOSURES BY THE INVENTOR

The first offer for sale of the new variety was August 2022 in the United States of America as published in 2023 Star® Roses and Plants Woody Ornamentals & Edibles Catalog. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Hydrangea* plant of the present invention was discovered through a controlled program during October 2012, at Cochranville, Pennsylvania. The objective of the controlled program was the development of *Hydrangea* cultivars that have improved growth habits and flowering capacity. The new *Hydrangea* cultivar is the result of mutagenized open pollinated seed from *Hydrangea paniculata* 'DVP Pinky' (U.S. Plant Pat. No. 16,166). The new cultivar was discovered and selected as a single flowering plant within the progeny of the above stated experiment during June 2017 in a controlled environment in Cochranville, Pennsylvania.

The new variety has been found to undergo asexual propagation in Cochranville, Pennsylvania by terminal stem cuttings since June 2017. Asexual propagation by terminal stem cuttings in Cochranville, Pennsylvania has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Hydrangea* plant of the present invention possesses the following combination of characteristics:

(a) forms bright white colored inflorescences which age from light pink to dark antique pink,
(b) provides very strong stems which prevent flopping, and
(c) displays a moderately vigorous, dense, and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, plants of the new cultivar are more floriferous with inflorescence color that ages more quickly to pink and an improved growth habit which is tighter and more compact compared to the 'DVP Pinky' variety (i.e., mutagenized seed parent). Moreover, the new variety can be readily distinguished from other similar non-parental varieties. For example, the 'Limelight' variety (U.S. Plant Pat. No. 12,874) bloom later and have a less compact and less tight growth habit compared to the new variety. In addition, the new cultivar produces inflorescences that age to pink sooner and develop a final inflorescence color that is darker than inflorescences of 'Limelight'.

The new variety has been named 'Pan1782hydr'.

BRIEF DESCRIPTION OF THE PHOTOGRAPH

The accompanying photograph of the drawing shows as nearly true as it is reasonably possible to make the same, in a color illustration of this character, a typical specimen of the plant parts of the new variety. Colors in the photograph differ slightly from the color values cited in the detailed description, which accurately describes the colors of 'Pan1782hydr'. The *Hydrangea* plant of the new variety was approximately four years of age and was observed during July 2021 while growing in a field at Cochranville, Pennsylvania, U.S.A.

The drawing sheet illustrates in the foreground a specimen of the plant of the new variety displaying the overall growth and flowering habit.

DETAILED BOTANICAL DESCRIPTION

The chart used in the identification of the colors is that of The Royal Horticultural Society (The R.H.S. Colour Chart, 2015 edition), London, England. The color values were determined in July 2022 under natural light conditions in Cochranville, Pennsylvania. The terminology which precedes reference to the chart has been added to indicate the corresponding color in more common terms. The description is based on the observation plants grown in three-gallon containers utilizing a soilless growth medium for 1 year in an outdoor nursery in Cochranville, Pennsylvania. Measurements and numerical values represent averages of typical plants.

Botanical classification: *Hydrangea paniculata* cultivar 'Pan1782hydr'.

Propagation:

*Type cutting*.—Terminal stem cuttings.

*Time to initiate roots during the summer*.—Approximately 24 days.

*Time to initiate roots during the winter*.—Approximately 30 days.

*Root description*.—White, medium thickness, fibrous.

*Rooting habit*.—Moderate branching and density.

Plant description:

*Commercial crop time*.—Approximately 12 months from a rooted cutting to finish in a 3-gallon pot.

*Growth habit and general appearance*.—Deciduous shrub, moderately vigorous, dense, and compact growth habit.

*Hardiness*.—USDA Zone 4.

*Size*.—Height from soil level to top of plant plane: Approximately 48.0 cm. Width: Approximately 60.0 cm.

*Branching habit*.—Freely branching. Pinching enhances branching. Quantity of lateral branches per plant: Approximately 9.

*Branch*.—Shape: Rounded. Strength: Very Strong. Length to base of inflorescence: Approximately 25.0 cm. Diameter: Approximately 8.0 mm. Length of central internode: Approximately 5.0 cm. Texture of young stem: Glabrous. Texture of mature stem: Woody. Color of young stem: commonly near Yellow-Green Group 146C. Color of mature stem: commonly near Greyed-Orange Group 165A.

*Lenticels*.—Quantity per internode: Approximately 47. Shape: Round to elliptic. Size: Approximately 0.5 mm to 1.0 mm. Color: commonly near Greyed-Orange Group 165A.

Foliage description:

*General description*.—Quantity of leaves per lateral branch: Approximately 6. Fragrance: None detected. Form: Simple. Arrangement: Opposite.

*Leaves*.—Aspect: Flat. Shape: Elliptic. Margin: Serrated. Apex: Acuminate. Base: Rounded. Venation pattern: Pinnate. Length of mature leaf: Approximately 15.0 cm. Width of mature leaf: Approximately 7.0 cm. Texture of upper and lower surfaces: Coriaceous, glabrous. Color of upper surface of young foliage: commonly near Green Group 137B with venation of near Green Group 143C. Color of lower surface of young foliage: commonly near Green Group 137D with venation of near Yellow-Green Group 146D. Color of upper surface of mature foliage: commonly near Green Group 139A with venation of near Yellow-Green Group 147B. Color of lower surface of mature foliage: commonly near Green Group 139C with venation of near Yellow-Green Group 147C. Anthocyanin coloration intensity: Strong.

*Petiole*.—Length: Approximately 2.0 cm. Diameter: Approximately 4.0 mm. Texture: Glabrous. Color: commonly near Yellow-Green Group 144A.

Flowering description:

*Flowering habit*.—Seasonal, continuously flowering from summer through fall in Cochranville, PA.

*Lastingness of individual inflorescence on the plant*.—Persistent.

Inflorescence description:

*General description*.—Type: Single fertile and sterile flowers arranged on large terminal panicles. Panicle Shape: Conical. Quantity per plant: One per lateral or sublateral stem. Fragrance: Noticeable light sweet scent. Aspect of sterile flowers: Face upward and outward. Height: Approximately 18.0 cm. Width: Approximately 17.0 cm. Quantity of fertile florets per inflorescence: Approximately 50. Quantity of sterile florets per inflorescence: Approximately 150. Conspicuousness of fertile flowers: Absent. Density of sterile flowers: Dense.

*Peduncle*.—Strength: Strong. Shape: Rounded. Length: Approximately 4.0 cm. Diameter: Approximately 3.0 mm. Texture: Moderately pubescent. Color: commonly near Yellow-Green Group 147C.

Floret description:

*General description*.—Type: Single, sterile and fertile flowers

*Sterile florets, bud just before opening*.—Shape: Globular. Length: Approximately 3.0 mm. Diameter: Approximately 3.0 mm. Color: commonly near Yellow-Green Group 145B.

*Sterile florets*.—Depth: Approximately 1.0 cm. Diameter: Approximately 3.5 cm.

*Sepals, sterile florets*.—Quantity: 4 to 5. Shape: Broadly obovate. Margin: Entire. Incision of margin presence: Absent. Apex: Broadly acute. Base: Cuneate. Attitude: Semi-erect. Overlapping of sepals: Very weak. Length: Up to 18.0 mm. Width: Up to 11.0 mm. Texture of upper and lower surfaces: Glabrous. Color of upper and lower surfaces when first open: commonly near White Group 155C. Color when mature and fading: commonly from near Red Group 51D to near Red-Purple Group 58A.

*Petals, sterile florets*.—Length: Approximately 1.6 cm. Width: Approximately 1.0 cm. Shape: Tear-drop. Color: Commonly near White Group NN155A.

*Pedicel, sterile florets*.—Strength: Strong. Aspect: Erect. Length: Approximately 1.5 cm. Diameter: Approximately 1.0 mm. Texture: Sparsely pubescent. Color: commonly near White Group 155C.

*Fertile florets, bud just before opening*.—Shape: Globular. Length: Approximately 3.0 mm. Diameter: Approximately 3.0 mm. Color: commonly near White Group 155C.

*Fertile florets*.—Depth: Approximately 5.0 mm. Diameter: Approximately 6.0 cm.

*Sepals, fertile florets*.—Length: Approximately 3.0 mm. Width: Approximately 2.0 mm. Shape: Elliptical. Color: Commonly near White Group NN155A.

*Petals, fertile florets*.—Shape: Lanceolate. Margin: Entire. Apex: Acute. Base: Truncate. Length: Approximately 3.0 mm. Width: Approximately 1.5 mm. Texture of upper and lower surfaces: Glabrous. Color of upper and lower surfaces when first open: commonly near White Group 155C.

*Pedicel, fertile florets*.—Strength: Strong. Aspect: Erect. Length: Approximately 1.0 mm. Diameter: Less than 1.0 mm. Texture: Glabrous. Color: commonly near White Group 155B.

*Reproductive organs*.—(Reproductive organs present only on fertile flowers; sterile flowers do not have reproductive organs) — Stamens: Quantity per flower: About ten. Anther shape: Round. Anther length: 3.0-5.0 mm. Anther color: 155A. Pollen: Very sparse, commonly near White Group 155C in color. Pistils: Pistil quantity per flower: Three, fused. Pistil length: Approximately 1.0 mm. Stigma shape: Oval, Stigma color: commonly near White Group 155A. Style length: Less than 1.0 mm. Style color: commonly near White Group 155A. Ovary color: commonly near Greyed- Green Group 193B.

Development:

*Seed and fruit production*.—Neither seed nor fruit production has been observed.

*Disease and pest resistance*.—Resistance to pathogens and pests common to *Hydrangea* has not been observed.

The new 'Pan1782hydr' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of *Hydrangea* plant named 'Pan1782hydr' characterized by the following combination of characteristics:

(a) forms bright white colored inflorescences which age from light pink to dark antique pink, (b) provides very strong stems which prevent flopping, and (c) displays a moderately vigorous, dense, and compact growth habit;

substantially as herein shown and described.

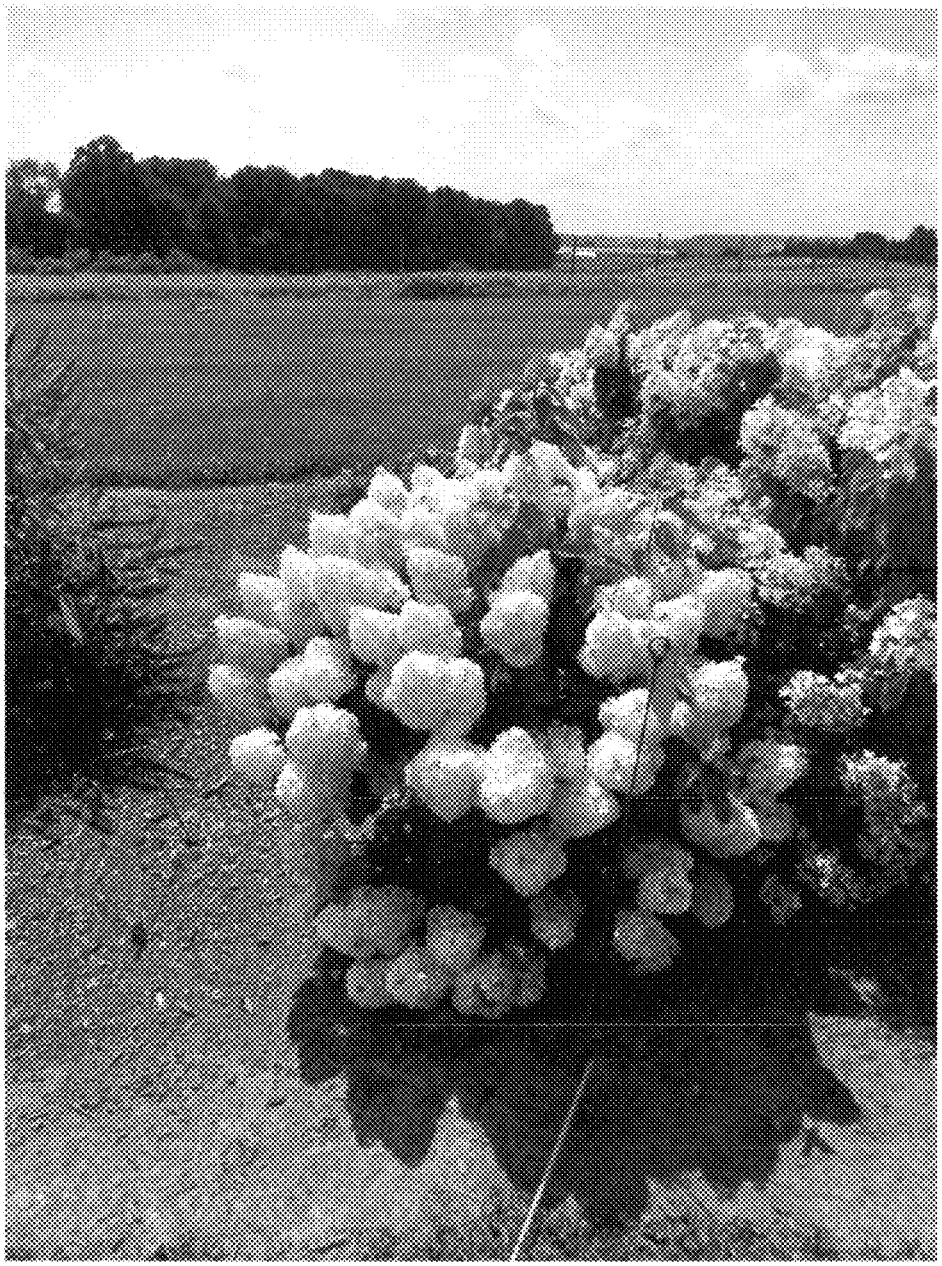

* * * * *